United States Patent [19]

Lewis, Jr.

[11] 4,360,011

[45] Nov. 23, 1982

[54] ADJUSTABLE WALKING IRON FOR LEG CASTS

[76] Inventor: Royce C. Lewis, Jr., 5233 W. 19th St., Lubbock, Tex. 79407

[21] Appl. No.: 194,567

[22] Filed: Oct. 6, 1980

[51] Int. Cl.³ .............................................. A61F 5/04
[52] U.S. Cl. .................................................... 128/83.5
[58] Field of Search ......................... 128/83.5, 83; 3/4

[56] References Cited

U.S. PATENT DOCUMENTS

| 2,762,367 | 9/1956 | Rubin | 128/83.5 |
| 2,966,154 | 12/1960 | Purcell | 128/83.5 |
| 3,481,332 | 12/1969 | Arnold | 128/83.5 |
| 3,877,423 | 4/1974 | Tollefsbol | 128/83.5 |

FOREIGN PATENT DOCUMENTS 2032540 1/1972 Fed. Rep. of Germany ..... 128/83.5

*Primary Examiner*—Kyle L. Howell
*Assistant Examiner*—C. W. Shedd
*Attorney, Agent, or Firm*—Marcus L. Bates

[57] ABSTRACT

A walking iron for attachment to the lower extremity of a foot or leg cast which bottom supports the limb and enables mobility of an injured person. The walking iron has a fixed, cast-engaging member adjustably connected to a ground-engaging member in such a manner that pivotal and longitudinal movement may be effected therebetween, thereby enabling lateral as well as fore and aft movement of one member respective to the other to be achieved. This expedient provides for center of gravity adjustment between the two members so that the walking iron can be specially fitted to each individual cast in the most optimum manner for each patient.

7 Claims, 5 Drawing Figures

U.S. Patent  Nov. 23, 1982  4,360,011
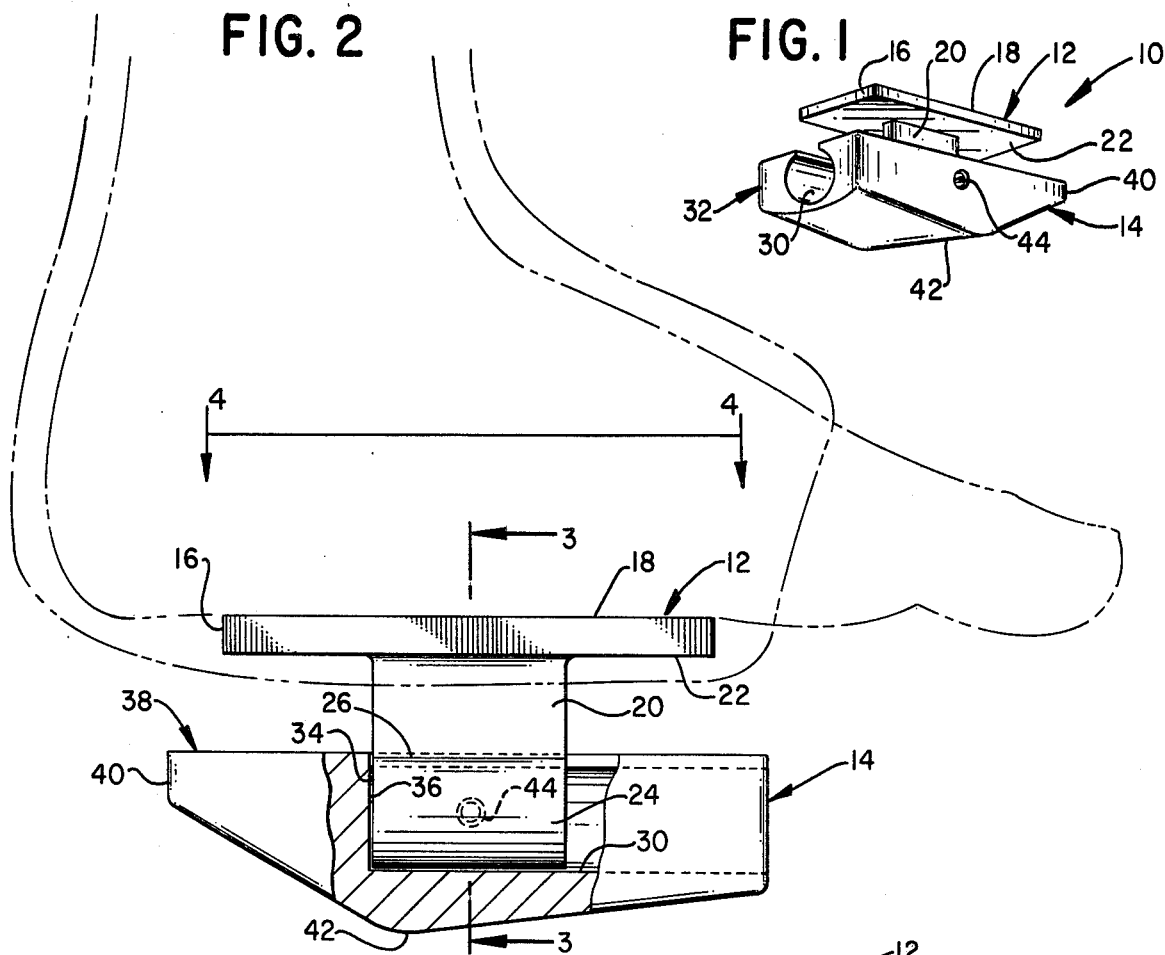
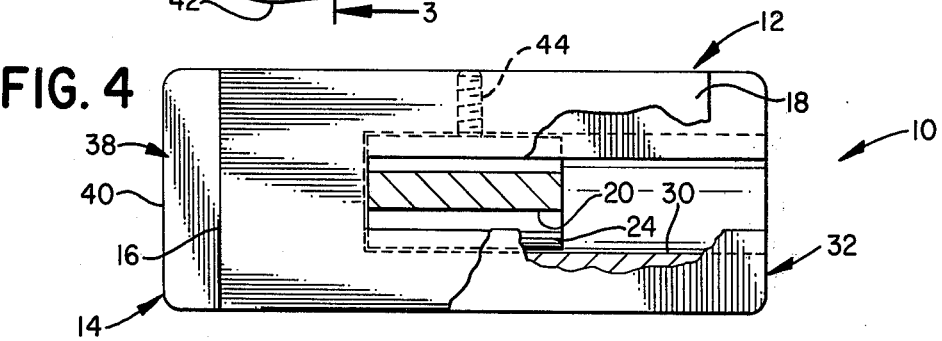
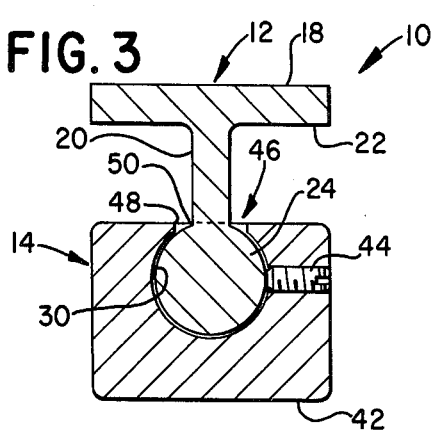
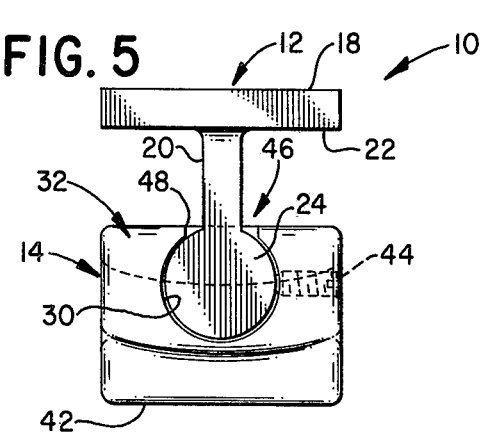

ADJUSTABLE WALKING IRON FOR LEG CASTS

BACKGROUND OF THE INVENTION

An injured lower extremity, such as the foot or leg, is conventionally placed in a cast. The cast may be a built-up composite of fabric material and plaster of Paris. The casts are fragile and easily damaged due to the frangible nature of this type of construction. In order to effect limited mobility of the patient, it is customary to affix a walking iron to the lower extremity of the cast in underlying relationship respective to the patient's foot so that the load presented by the mass of one's body can be safely transferred into the cast and thence into the walking iron. Hence the walking iron is arranged to effectively bottom support the cast to avoid direct application of undesirable forces to the immediate bottom of the foot, and to avoid concentration of destructive loads to isolated or small areas of the cast.

After a cast is fitted, with the walking iron being made integrally therewith, subsequent adjustment cannot usually be effected. Moreover, transfer of loads from the cast into the ground has not heretofore received significant study; and therefore, it would be desirable to improve the configuration of the ground-contacting part of the prior art walking iron, as well as providing for the before mentioned adjustment, and such a desirable walking iron is the subject of this invention.

Mention is made of U.S. Pat. Nos. 2,966,154; 2,401,068; 1,383,928; 2,264,570; and 2,762,367 for further background of this invention.

SUMMARY OF THE INVENTION

An improved walking iron for use in conjunction with a leg or foot cast. The walking iron includes a fixed member made integrally with the bottom of the cast and a ground-engaging member pivotally and slidably affixed in underlying cooperative relationship to the fixed member so that longitudinal and lateral adjustment therebetween can be easily effected.

The fixed member has an upper flange for attachment to the cast in underlying relationship to the sole of one's foot. A web member is integrally attached to the lower side of the flange and extends in opposition to the sole side thereof.

The ground engaging adjustable member is specially configured for improved ground engagement which enhances "feel" and "balance" of the patient. The lower side of the adjustable member is curved in a special manner and presents a lowermost contact area positioned favorably respective to the patient's center of gravity, and to the shifting or changing motion which results from the stride or walking motion peculiar to the individual.

Adjustment between the fixed and adjustable members is effected by a cylinder which is slidably received within a complementary socket arranged to enable longitudinal and lateral pivotal movement therebetween so that the entire assembly can be subsequently adjusted for the optimum comfort of the patient.

Therefore, a primary object of the present invention is the provision of improvements in a walking iron for casts which is of two-piece construction mated in a manner to effect subsequent adjustment therebetween which maximizes the comfort or minimizes the discomfort of the user.

Another object of the invention is to provide a walking iron having a lower, ground-contacting member of a configuration which optimumly distributes the weight of the user.

A further object of this invention is to disclose and provide a walking iron of two-piece construction which is laterally adjusted to enhance the utility thereof.

A still further object of this invention is to provide a walking iron having an improved, ground-contacting lower member adjustably connected to a cast-engaging upper member in an unusual manner which provides unexpected results heretofore unattainable.

Another and still further object of this invention is the provision of a walking iron which distributes the mass of the user in a more comfortable and advantageous manner.

An additional object of this invention is to disclose and provide a walking iron which is of two-piece construction and which has a ground-contacting member adjustably affixed to a cast-engaging member in such a manner that the members are adjustable respective to one another in both a lateral and longitudinal direction, and which enables consideration of the weight distribution of people of various different size and shape.

These and various other objects and advantages of the invention will become readily apparent to those skilled in the art upon reading the following detailed description and claims and by referring to the accompanying drawings.

The above objects are attained in accordance with the present invention by the provision of a combination of elements which are fabricated in a manner substantially as described in the above abstract and summary.

BRIEF DESCRIPTION OF THE DRAWINGS

FIG. 1 is a perspective view of a walking iron made in accordance with the present invention;

FIG. 2 is an enlarged, side elevational view of the apparatus disclosed in FIG. 1, with some parts thereof being broken away and the remaining parts shown in cross-section in order to disclose the interior thereof;

FIG. 3 is a cross-sectional view taken along line 3—3 of FIG. 2;

FIG. 4 is a top plan view of the apparatus disclosed in FIGS. 1-3, with some parts being broken away therefrom, and some of the remaining parts being shown in cross-section; and, FIG. 5 is an end view of the apparatus disclosed in the foregoing figures.

DETAILED DESCRIPTION OF THE PREFERRED EMBODIMENT

In FIG. 1 there is disclosed a walking iron 10 made in accordance with the present invention, and which includes a cast-engaging and therefore fixed member 12 and a ground-engaging member 14 adjustably attached thereto.

As seen in FIGS. 1-5, the walking iron of this invention includes an upper plate 16 which is elongated and more or less rectangular in form for bottom supporting a cast predominately from a bearing pressure effected between the underside of a cast and the upper face 18 of the plate. The lower face 22 of the plate is opposed to the upper face. Web member 20 is integrally attached to the plate and downwardly extends or depends therefrom. The web preferably is elongated and of relatively thin section, and its function is to suitably space pivot member 24 from the plate, while at the same time enabling wrapping of fabric thereabout so as to permanently anchor the cast-engaging member to the lower end of a built-up cast.

Member 24 is an enlargement which is joined at 26 to the lower end of the web. The enlargement preferably is in the form of an elongated cylinder having an end wall 28 looking through a complementary counterbore 30. The cylinder and counterbore jointly cooperate to form a socket of close tolerance slidable fit respective to one another.

The toe or forward end 32 of the pivotal or ground-engaging member 14 receives the counterbore. The counterbore extends into the pivotal member and is terminated by bulkhead 36 which abuttingly engages the heel or trailing end 34 of the cylinder when the fixed member and pivotal member are in one extreme position of adjustment.

As best illustrated in FIG. 3, together with other figures of the drawings, the longitudinally disposed counterbore upwardly opens through the upper face 38 of the pivotal member and therefore is discontinuous in that the inside wall surface thereof terminates at about 320° or so rather than continuing for 360° as might be true with the more familiar continuous counterbore.

Heel end 40 of the ground engaging member is spaced from toe end 32. The lowermost ground-contacting surface 42 is generally the first portion of the walking iron to engage the ground in normal use. The lower ground-contacting face of the pivotal member upwardly and outwardly curves towards the toe and heel ends thereof with contact part 42 lying more rearwardly respective to the heel end as compared to the toe end.

Adjusting screw 44 prevents pivotal and longitudinal movement of the cylinder respective to the counterbore, or the fixed member respective to the pivotal member. Gap 46 is formed by spaced, longitudinally extending edges 48 of the termination of the counterbore or spaced discontinuous socket walls. The joinder of the web and cylinder integrally occurs at 26 with the spaced distance between the general location 50 and 48 being ample to achieve any desired degree of pivotal action or motion necessary for maximizing the comfort and therapeutic advantages found herein.

In use, the fixed member is slidably separated from the pivotal member, thereby enabling unhindered application of cast material as the plate 18 is incorporated as an integral lower part of the composite cast. After the cast has hardened, the pivotal member is slidably mated to its coacting fixed member and the set screw tightened to secure one member to the other. At this time, the patient usually is recumbent and only a rough estimated adjustment is effected to the coacting parts. When the patient attains an ambulatory condition, final adjustment is effected to more nearly optimize the alignment of the initial ground contact point 42 respective to the patient's center of gravity and walking peculiarities. This entails effecting the proper longitudinal alignment as well as the pivotal relationship between the two members.

As the patient learns to walk in his cast, a more natural placement of his foot on the ground is achieved because of the configuration of member 14, together with the unusual adjustment features of the present invention. Initial contact will be made with the ground at a location slightly rearwardly on the curved area 42, with the member then rocking forwardly over the entire area 42 where the walking iron will then leave the ground as contact is lost at a location forwardly of 42; and, thereafter contact with the ground is again made during the next stride in the above described manner as one walks about in his cast using the present invention.

After final adjustment has been made to the invention, a second drilled passageway can be made through the pivotal member and into the cylinder. A self-tapping screw is next fitted therein, thereby precluding the possibility of damage should the set screw 44 inadvertently become loosened.

Additionally, a splined connection can be utilized between the coacting surfaces of the cylinder and counterbore, with the attendent loss of an infinite number of adjustment locations in preference to a finite number of lateral adjustment locations.

Anti-skid material, along with various thin padding, can be layered onto the bottommost surface where deemed desirable. The component parts of this walking iron may be fabricated by injection molding using either plastic or aluminum. It is preferred to employ plastic, such as PVC, and it is considered obvious to provide lightening holes in the main body portions in order to conserve both weight and cost, as well as to use variations in the design of the various components thereof. The illustration found in the drawings is therefore but one selected embodiment of many different embodiments of this invention.

I claim:

1. A walking iron for use in conjunction with a cast applied to one's lower extremity, such as ones foot, comprising: a cast-engaging fixed member; a ground-engaging member;

said ground-engaging member includes a main body having opposed sides, a toe end, a heel end, a lowermost ground-engaging surface, and an uppermost end portion;

said fixed member includes an upper and a lower face and which can be integrally incorporated into a cast applied to one's foot such that the upper surface of the fixed member can bottom support the lower end of a cast, thereby transferring a load from a limb, into the fixed member, and into the ground-engaging member;

a web member affixed to the lower face of said fixed member which downwardly extends therefrom and terminates in a longitudinally extending enlargement; said longitudinally extending enlargement includes an axial centerline extending generally in a direction from said toe towards said heel;

means forming a cavity within said ground-engaging member for slidably receiving said enlargement therewithin, so that said ground-engaging member can be pivotally moved respective to said fixed member; a gap formed within said uppermost end portion of said ground-engaging member by which said cavity upwardly opens; said web extends through said gap;

and fastener means by which said fixed and ground-engaging members are rigidly fastened to one another.

2. The walking iron of claim 1 wherein said enlargement is a cylinder, said cavity is a counterbore formed in the uppermost end portion of said ground-engaging member for receiving said cylinder therewithin so that the ground-engaging member can be pivotally moved sidewise respective to said cast-engaging fixed member.

3. The walking iron of claim 1 wherein said fixed member has a substantially flat, foot-engaging upper face, said web is a vertical member which terminates in an elongated cylindrical enlargement, the axial centerline of said cylinder extends generally along a path which lies parallel to the plane of the upper face of said fixed member.

4. A walking iron for incorporation into the lower extremity of a cast applied to one's foot, comprising:
a cast-engaging fixed member and a ground-engaging adjustable member; said fixed and adjustable members are connected together by an adjustment means which allows pivotal movement in a lateral direction therebetween;
said fixed member includes an upper platform member which can be integrally affixed to the lower extremity of a cast, a web member having one end affixed to and downwardly extending from said platform, the opposed end of said web member is affixed to an elongated enlargement;
said adjustable member includes a ground-engaging lower end and an upper end pivotally connected to said enlargement by said adjustment means;
said adjustment means includes an elongated counterbore formed in said adjustable member and made complementary respective to said enlargement, so that said enlargement is slidably received in a pivotal manner within said counterbore;
and fastener means by which said adjustable member is fixed respective to said fixed member.

5. The walking iron of claim 4 wherein said adjustable member includes a toe end spaced from a heel end, a lower ground-contacting surface located below and spaced from said toe and heel end which upwardly and outwardly extends towards said toe and heel ends.

6. The walking iron of claim 5 wherein said enlargement includes a longitudinally extending cylinder having an axial centerline extending generally in a direction from said toe towards said heel; said web member terminates in said cylinder.

7. The walking iron of claim 4 wherein said web is a vertical member which terminates in an elongated cylindrical enlargement, the axial centerline of said cylinder extends generally along a path which lies parallel to the plane of the upper platform member
a gap formed in the upper end of said ground-engaging member loosely receives said web therethrough, said counterbore receives the cylinder in close tolerance relationship therewithin;
and said fastener means releasably fastens the ground-engaging member with respect to the cylinder.

* * * * *